United States Patent [19]

Bolich, Jr. et al.

[11] 4,323,683

[45] Apr. 6, 1982

[54] PROCESS FOR MAKING PYRIDINETHIONE SALTS

[75] Inventors: Raymond E. Bolich, Jr., Maineville; Steven A. Shaya, Cincinnati; Christian Steuri, Fairfield, all of Ohio

[73] Assignee: The Procter & Gamble Company, Cincinnati, Ohio

[21] Appl. No.: 119,346

[22] Filed: Feb. 7, 1980

[51] Int. Cl.$^3$ .............................................. C07D 213/89
[52] U.S. Cl. .......................................... 546/6; 546/243
[58] Field of Search ...................................... 546/6, 243

[56] References Cited

U.S. PATENT DOCUMENTS

| | | | |
|---|---|---|---|
| 2,286,847 | 3/1957 | Cislak | 260/294.8 |
| 2,809,971 | 10/1957 | Bernstein | 260/270 |
| 3,037,849 | 6/1962 | Frint et al. | 23/200 |
| 3,583,999 | 6/1971 | Damico | 260/294.8 G |
| 3,590,035 | 6/1971 | Damico | 260/290 |
| 3,773,770 | 11/1973 | Damico | 260/290 R |
| 3,836,531 | 9/1974 | Yano | 544/182 |
| 4,089,945 | 5/1978 | Brinkman | 424/164 |

OTHER PUBLICATIONS

Barnett et al. Inorg. Chem 16, 1834 (1977).
Troost, Chem. Abs. 71, 16745y (1968).
Despotovic et al., Chem. Abs. 87, 76469b (1976).
Blinova et al., Chem. Abs. 76, 145848m.

*Primary Examiner*—Mark L. Berch
*Attorney, Agent, or Firm*—Douglas C. Mohl; John V. Gorman; Richard C. Witte

[57] ABSTRACT

A process for producing heavy metal, magnesium or aluminum pyridinethione salt crystals involving reacting a water soluble salt of the desired metal with a water soluble pyridinethione salt or pyridinethione itself in an aqueous surfactant medium.

11 Claims, No Drawings

PROCESS FOR MAKING PYRIDINETHIONE SALTS

TECHNICAL FIELD

The present invention relates to the formation of heavy metal, magnesium or aluminum pyridinethione salts. Such salts are useful as antidandruff agents. Up to this time the pyridinethione salts have been in such a form that they interfered with the ability of pearlescent materials to deliver pearlescence to compositions containing both materials.

BACKGROUND ART

Pyridinethione salts are old as shown by U.S. Pat. No. 2,809,971, Oct. 15, 1957 to Bernstein et al. Other patents disclosing similar compounds and processes for making them include U.S. Pat. Nos. 2,786,847, Mar. 26, 1957 to Cislak and 3,583,999, June 8, 1971; 3,590,035, June 29, 1971; and 3,773,770, Nov. 20, 1973 all to Damico.

While the prior art discloses pyridinethione salts and processes for making such salts, it does not suggest forming the salts in an aqueous surfactant medium. Furthermore, there is no suggestion that the crystals formed in such a medium would have superior aesthetic properties and be more compatible in a composition.

It is, therefore, an object of the present invention to provide an improved method for making pyridinethione salt crystals.

It is a further object of the present invention to provide pyridinethione salt crystals which are more compatible in pearlescent cosmetic compositions.

These and other objects will become apparent from the description of the invention which follows.

SUMMARY OF THE INVENTION

The present invention relates to the formation of heavy metal, magnesium or aluminum pyridinethione salt crystals by reacting pyridinethione or a water soluble pyridinethione salt with a water soluble salt of the desired metal in an aqueous surfactant medium. The concentration of surfactant is not critical but is preferably from about 1% to about 24%, more preferably from about 1% to about 8%. The reaction temperature is at least about 20° C., preferably from about 60° C. to about 100° C. The crystals may be separated from the reaction medium after formation for use in a particular formulation not containing the surfactant used in the reaction. Alternatively, if desired, the crystals may be left in the reaction medium for incorporation into a final composition.

DETAILED DESCRIPTION OF THE INVENTION

The process of the present invention involves the steps enumerated supra. The reactants can be handled in a wide variety of ways. For example, the water soluble salt of the desired metal may be combined with part of the surfactant and water while the remainder of the water and surfactant are combined with pyridinethione or a water soluble pyridinethione salt. The two mixtures are then combined. Alternatively, all of the surfactant may be combined with either material or put into a third container into which the materials are then placed. All of these approaches are satisfactory since the crystals form almost instantaneously regardless of the approach used.

The crystals possess a median equivalent spherical diameter based on volume, $\bar{d}_v$, and a mean sphericity $$\psi = \left(\frac{\bar{d}_v}{\bar{d}_s}\right)^2 \text{ or}$$

surface area of spheres having an equivalent volume distribution divided by the actual surface area of the particles as measured which makes them more compatible with other pearlescent materials which may be present in a composition. The median equivalent diameter is preferably greater than $2\mu$ while the mean sphericity is preferably in the range of about 0.20 to about 0.65.

The various reaction materials are discussed in detail below.

Pyridinethione and Water Soluble Pyridinethione Salts

Pyridinethione as the term is used herein is 1-hydroxy-2-pyridinethione which has the following structural formula in tautomeric form, the sulfur being attached to the No. 2 position in the pyridine ring.

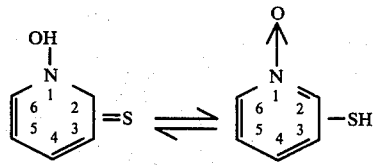

The water soluble salts represent substitution of the metal cation for the hydrogen of one of the tautomeric forms. The preferred salts are those involving ammonium or alkali metals. Most preferred is the sodium salt.

The amount of 1-hydroxy-2-pyridinethione or water soluble salt can vary over a wide range (the level only dependent on the quantity of material desired). A preferred level is from about 8% to about 16% of the total reaction system.

Water Soluble Salt Of A Heavy Metal, Magnesium or Aluminum

Suitable metal compound reactants include salts in which the metal may be, among others heavy metals such as, zinc, tin, cadmium and zirconium, magnesium and aluminum. The compounds may be nitrates, acetates, sulfates or halogens. The preferred salts are sulfates and zinc sulfate is the most preferred. The amount of soluble metal salt used is not critical so long as the amount is sufficient to form the desired pyridinethione salt. The amount used therefore is generally an amount sufficient to provide a stoichiometric excess. An excess of about 5% is an example of a suitable excess amount.

Surfactant

Another necessary component in the process of the present invention is a surfactant. The term "surfactant" as used herein is intended to denote soap and nonsoap surfactants. Any nonsoap surfactant is suitable for use including anionic, nonionic, amphoteric, cationic and zwitterionic types. The surfactant should be soluble in water at the temperature of the reaction.

Examples of suitable soaps are the sodium, potassium, ammonium and alkanol ammonium salts of higher fatty acids (those having 10-20 carbon atoms). Anionic nonsoap surfactants can be exemplified by the alkali metal salts of organic sulfuric reaction products having in their molecular structure an alkyl radical containing from 8–22 carbon atoms and a sulfonic acid or sulfuric acid ester radical (included in the term alkyl is the alkyl portion of higher acyl radicals). Preferred are the sodium, ammonium, potassium or triethanol amine alkyl sulfates, especially those obtained by sulfating the higher alcohols ($C_8$–$C_{18}$ carbon atoms), sodium coconut oil fatty acid monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water soluble salts of condensation products of fatty acids with sarcosine; and others known in the art.

Nonionic surfactants can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propyelene oxide, said base having a molecular weight of the order of 2,500 to 3,000, are satisfactory.

3. The condensation product of aliphatic alcohols having from 8 to 18 carbon atoms, in either straight chain or branched chain configuration, with ethylene oxide, e.g., a coconut alcohol ethylene oxide condensate having from 10 to 30 moles of ethylene oxide per mole of coconut alcohol, the coconut alcohol fraction having from 10 to 14 carbon atoms.

4. Long chain tertiary amine oxides corresponding to the following general formula:

$$R_1R_2R_3N \rightarrow O$$

wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyldodecylamine oxide, oleyldi (2-hydroxyethyl)amine oxide, dimethyloctylamine oxide, dimethyldecylamine oxide, dimethyltetradecylamine oxide, 3,6,9-trioxaheptadecyldiethylamine oxide, di)2-hydroxyethyl)-tetradecylamine oxide, 2-dodecoxyethyldimethylamine oxide, 3-dodexocy-2-hydroxypropyldi(3-hydroxypropyl)amine oxide, dimethylhexadecylamine oxide.

5. Long chain tertiary phosphine oxides corresponding to the following general formula:

$$RR'R''P \rightarrow O$$

wherein R contains an alkyl, alkenyl or monohydroxyalkyl radical ranging from 8 to 18 carbon atoms in chain length, from 0 to about 10 ethylene oxice moieties and from 0 to 1 glyceryl moiety and R' and R" are each alkyl or monohydroxyalkyl groups containing from 1 to 3 carbon atoms. Examples of suitable phosphine oxides are:

dodecyldimethylphosphine oxide,
tetradecyldimethylphosphine oxide,
tetradecylmethylethylphosphine oxide,
3,6,9-trioxaoctadecyldimethylphosphine oxide,
cetyldimethylphosphine oxide,
3-dodecoxy-2-hydroxypropyldi(2-hydroxyethyl)-phosphine oxide,
stearyldimethylphosphine oxide,
cetylethylpropylphosphine oxide,
oleyldiethylphosphine oxide,
dodecyldiethylphosphine oxide,
tetradecyldiethylphosphine oxide,
dodecyldipropylphosphine oxide,
dodecyldi(hydroxymethyl)phosphine oxide,
dodecyldi(2-hydroxyethyl)phosphine oxide,
tetradecylmethyl-2-hydroxypropylphosphine oxide,
oleyldimethylphosphine oxide,
2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include:

octadecyl methyl sulfoxide,
2-ketotridecyl methyl sulfoxide,
3,6,9-trioxaoctadecyl 2-hydroxyethyl sulfoxide, dodecyl methyl sulfoxide,
oleyl 3-hydroxypropyl sulfoxide,
tetradecyl methyl sulfoxide,
3-methoxytridecyl methyl sulfoxide,
3-hydroxytridecyl methyl sulfoxide,
3-hydroxy-4-dodecoxybutyl methyl sulfoxide.

Zwitterionic surfactants can be exemplified by those which can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

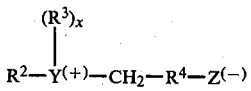

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; $R^3$ is an alkyl or monohydroxyalkyl group containing 1 to about 3 carbon atoms; X is 1 when Y is a sulfur atom and 2 when Y is a nitrogen or phosphorus atom; $R^4$ is an alkylene or hydroxyalkylene of from 1 to about 4 carbon atoms and Z is a radical selected from the group consisting of carboxylate, sulfonate, sulfate, phosphonate, and phosphate groups.

Examples include:
4-[N,N-di(2-hydroxyethyl)-N-octadecylammonio]-butane-1-carboxylate;
5-[S-3-hydroxypropyl-S-hexadecylsulfonio]-3-hydroxypentane-1-sulfate;
3-[P,P-diethyl-P-3,6,9-trioxatetradexocylphosphonio]-2-hydroxypropane-1-phosphate;
3-[N,N-dipropyl-N-3-dodecoxy-2-hydroxypropylammonio]-propane-1-phosphonate;
3-(N,N-dimethyl-N-hexadecylammonio)propane-1-sulfonate;
3-(N,N-dimethyl-N-hexadecylammonio)-2-hydroxypropane-1-sulfonate;
4-]N,N-di(2-hydroxyethyl)-N-(2-hydroxydodecyl)ammonio]-butane-1-carboxylate;
3-[S-ethyl-S-(3-dodecoxy-2-hydroxypropyl)sulfonio]-propane-1-phosphate;
3-(P,P-dimethyl-P-dodecylphosphonio)-propane-1-phosphonate; and
5-[N,N-di(3-hydroxypropyl)-N-hexadecylammonio]-2-hydroxypentane-1-sulfate.

Examples of amphoteric surfactants which can be used in the process of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378.

Many cationic surfactants are known to the art. By way of example, the following may be mentioned:
dodecyltrimethylammonium chloride;
nonylbenzylethyldimethylammonium nitrate;
tetradecylpyridinium bromide;
laurylpyridinium chloride;
cetylpyridinium chloride;
laurylpyridinium chloride;
laurylisoquinolium bromide;
dilauryldimethylammonium chloride; and
stearalkonium chloride.

Many additional nonsoap surfactants are described in McCUTCHEON'S, DETERGENTS AND EMULSIFIERS, 1979 ANNUAL, published by Allured Publishing Corporation, which is incorporated herein by reference.

The above-mentioned surfactants can be used alone or in combination in the process of the present invention. The surfactant concentration, as noted earlier, is not critical but is preferably from about 1% to about 24%, more preferably from about 1% to about 8%.

Reaction Temperature

The reaction temperature should be above about 20° C., preferably from about 60° C. to about 100° C. The temperature can be achieved and maintained through the use of any of the techniques well known in the art.

Reactant Medium

The process of the present invention is carried out in an aqueous medium wherein water is the major diluent.

Industrial Applicability

The pyridinethione salts made in accordance with the present process are useful in hair care compositions as antidandruff agents.

The following Examples further describe and demonstrate the preferred embodiments within the scope of the present invention. The Examples are given solely for the purpose of illustration and are not to be construed as limitations of the present invention as many variations thereof are possible without departing from its spirit and scope. Unless otherwise indicated, all percentages herein are by weight.

EXAMPLE I

Zinc pyridinethione salt crystals of the present invention were made using the following procedure.

A first mixture was prepared by combining 14.7 parts of zinc sulfate, 21.7 parts of a 29% aqueous solution of sodium alkyl sulfate and 8.6 parts of water in a mix tank. This mixture was heated to 95° C.

A second mixture was prepared by combining 35 parts of a 40% aqueous solution of sodium pyridinethione with 20 parts of a 29% aqueous solution of sodium alkyl sulfate in a mix tank. This second mixture was also heated to 95° C.

The first mixture was added to the second mixture resulting in the formation of zinc pyridinethione crystals which were washed and collected.

The total batch size, the combined mixtures, was 2500 grams.

EXAMPLE II

The crystals of zinc pyridinethione made according to Example I were evaluated to determine their particle size and sphericity.

The median equivalent spherical diameter based on volume (particle size) was determined by means of a SediGraph 5000 D Particle Size Analyzer supplied by Micrometrics Instrument Corporation.

The SediGraph 5000 D determines, by means of X-ray absorption, the concentration of particles remaining at decreasing sedimentation depths as a function of time. Stokes' Law relates the measured equilibrium velocity of a particle falling through a viscous medium to its equivalent spherical diameter (ESD).

$$ESD = \left[\frac{18 \cdot \eta \cdot \nu}{(\rho - \rho_o)g}\right]^{\frac{1}{2}}$$

$\eta$ = liquid viscosity
$\nu$ = equilibrium velocity
$\rho_o$ = liquid density
g = gravitational acceleration
$\rho$ = particle density $\nu$ is determined from the Sedigraph while the other variables are available from reference sources or obtained experimentally. In the present analysis water was the liquid and the liquid viscosity was 0.76 cp.

The density of zinc pyridinethione particles is known to be about 1.81 g/cc, (Barnett, B. L., et al, "Structural Characterization of Bis-(N-oxypyridine-2-thionato) Zinc (II)", *Inorganic Chemistry* 16, 1834, [1977]), incorporated herein by reference.

The median equivalent spherical diameter based on volume ($\bar{d}_v$) of the crystals was determined to be 5.4μ. This median equivalent spherical diameter was taken from the mass distribution of particles described in 1. below. The determination of a specific surface area based on equivalent spherical diameters was as follows:

1. A cumulative mass distribution of equivalent spherical diameters in μm was obtained using the SediGraph instrument described previously. The rate for the instrument was 866 and the starting diameter of 100 μm.
2. The cumulative mass distribution was divided into equal logarithmic intervals in μm. The sizes of the intervals are shown in the following table.
3. The cumulative mass distribution at each equal logarithmic interval was determined.
4. The diameter at the centerpoint of each interval was determined.
5. The value of the cumulative mass percent distribution at the centerpoints of the intervals was determined.
6. The value of the differential mass percent distribution was then determined.
7. The amount of material for each interval was determined, assuming that there was a total of one gram which was evaluated. These values are the values in 6, above, divided by 100.
8. The assumed spherical particle surface area of the material contained in each interval was calculated using diameters equal to the centerpoints of the intervals. Therefore, the calculation for a particular interval, i, is $$A_i = \frac{\text{(Mass contained in interval } i\text{)}}{\text{(Mass of sphere with diameter } d_i\text{)}^x}$$

(Surface area of sphere with diameter $d_i$)

$$A_i = \frac{\text{Mass contained in interval } i}{\rho \, 4/3 \, \pi \left(\frac{d_i}{2}\right)^3} (d_i)^2 \pi = \frac{6}{\rho} \frac{\text{mass}}{d_i}$$

$A = \Sigma_i A_i$ = Surface area/g assuming spheres

All of the above data are shown in the following table. The numerical column headings correspond to the numbers above.

| 2 | 3 | 4 | 5 | 6 | 7 | 8 |
|---|---|---|---|---|---|---|
| 1.59 | 0. | | | | | |
| | | 1.78 | 0.5 | 0.5 | 0.005 | 0.009 |
| 2.00 | 1.0 | | | | | |
| | | 2.28 | 2.5 | 2.0 | 0.020 | 0.029 |
| 2.52 | 4.0 | | | | | |
| | | 2.87 | 7.0 | 4.5 | 0.045 | 0.052 |
| 3.17 | 10.0 | | | | | |
| | | 3.59 | 16.0 | 9.0 | 0.090 | 0.083 |
| 4.00 | 22.0 | | | | | |
| | | 4.52 | 32.0 | 16.0 | 0.160 | 0.118 |
| 5.04 | 42.0 | | | | | |
| | | 5.70 | 55.0 | 23.0 | 0.230 | 0.134 |
| 6.35 | 68.0 | | | | | |
| | | 7.18 | 76.0 | 21.0 | 0.210 | 0.097 |
| 8.00 | 84.0 | | | | | |
| | | 9.04 | 88.5 | 12.5 | 0.125 | 0.046 |
| 10.08 | 93.0 | | | | | |
| | | 11.4 | 95.0 | 6.5 | 0.065 | 0.019 |
| 12.7 | 97.0 | | | | | |
| | | 14.4 | 98.0 | 3.0 | 0.030 | 0.007 |
| 16.0 | 99.0 | | | | | |
| | | 18.1 | 99.5 | 1.5 | 0.015 | 0.003 |
| 20.2 | 100.0 | | | | | |
| | | 22.8 | 100.0 | 0.5 | 0.005 | 0.001 |
| 25.4 | 100.0 | | | | | |
| | | TOTAL | 100.0 | | 1.000 g | 0.598 m²/g |

The actual specific surface area for the crystals was determined by means of a B.E.T. surface area analysis using nitrogen gas. The B.E.T. analysis showed the crystals to have a specific surface area of 2.39 m²/g.

The sphericity was then determined as follows:

$$\psi = \frac{\text{area per g calculated for assumed spherical distribution}}{\text{area per g from B.E.T. measurement}}$$

$$\psi = \frac{0.598}{2.39} = 0.25$$

EXAMPLE III

Zinc pyridinethione salt crystals were made using the following process of the present invention.

A first mixture was prepared by combining 7.3 parts of a 28% aqueous solution of ammonium alkyl sulfate, 2 parts of zinc sulfate and 40.7 parts of water in one mix tank. The mixture was heated to 80° C.

A second mixture was prepared by combining 7.3 parts of a 28% aqueous solution of ammonium alkyl sulfate, 5 parts of a 40% aqueous solution of sodium pyridinethione and 37.7 parts of water in another mix tank. This mixture was also heated to 80° C.

The first and second mixtures were metered into a third tank at the rate of 1 kg./min. The resulting zinc pyridinethione crystals were washed and stored.

What is claimed is:

1. A process for making heavy metal, magnesium or aluminum N-hydroxy pyridinethione salts comprising reacting 1-hydroxy-2-pyridinethione or a water soluble salt thereof with a water soluble heavy metal, magnesium or aluminum salt in an aqueous surfactant medium, wherein the reaction temperature is at least about 20° C.

2. A process according to claim 1 wherein the pyridinethione compound is an alkali metal pyridinethione salt and the concentration of surfactant in the total reaction mixture is from about 1% to about 24%.

3. A process according to claim 2 wherein the metal salt is a heavy metal salt selected from the group consisting of zinc, tin, cadmium and zirconium salts and is present in an amount sufficient to provide a stoichiometric excess.

4. A process according to claim 3 wherein the surfactant is anionic.

5. A process according to claim 4 wherein the heavy metal salt is a zinc salt.

6. A process according to claim 5 wherein the reaction temperature is from about 60° C. to about 100° C.

7. A process according to claim 6 wherein the concentration of surfactant is from about 1% to about 8%.

8. A process according to claim 7 wherein the alkali metal pyridinetione salt is sodium pyridinethione.

9. A process according to claim 8 wherein the zinc salt is zinc sulfate.

10. A process according to claim 9 wherein the anionic surfactant is an alkyl sulfate.

11. A process according to claim 10 wherein the alkyl sulfate is sodium alkyl sulfate.

* * * * *